(12) United States Patent
Hillen et al.

(10) Patent No.: US 6,541,233 B1
(45) Date of Patent: Apr. 1, 2003

(54) β-GLUCANASE FROM A BACILLUS

(75) Inventors: Wolfgang Hillen, Erlangen (DE); Karl-Heinz Mauer, Erkrath (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/463,862

(22) PCT Filed: Jul. 21, 1998

(86) PCT No.: PCT/EP98/04564

§ 371 (c)(1),
(2), (4) Date: May 1, 2000

(87) PCT Pub. No.: WO99/06573

PCT Pub. Date: Feb. 11, 1999

(30) Foreign Application Priority Data

Jul. 30, 1997 (DE) .......................... 197 32 751

(51) Int. Cl.⁷ .............................. C12N 9/36; C12N 9/00; C12N 1/20; C07H 21/04
(52) U.S. Cl. .................. 435/206; 435/69.1; 435/183; 435/200; 435/201; 435/202; 435/203; 435/204; 435/205; 435/206; 435/207; 435/208; 435/209; 435/211; 435/252.3; 435/262; 435/264; 435/288.4; 435/252.5; 536/23.2; 536/23.7
(58) Field of Search ................ 435/69.1, 183, 435/200, 201–206, 207, 208, 209, 210, 211, 252.3, 252.5, 262, 264, 288.4; 536/23.2, 23.7

(56) References Cited

U.S. PATENT DOCUMENTS

| | | | |
|---|---|---|---|
| 4,585,642 A | 4/1986 | Rieck | 423/333 |
| 4,664,839 A | 5/1987 | Rieck | 252/175 |
| 4,820,439 A | 4/1989 | Rieck | 252/135 |
| 4,966,996 A | 10/1990 | Schaefer et al. | 562/598 |
| 4,985,553 A | 1/1991 | Fuertes et al. | 536/124 |
| 5,183,651 A | 2/1993 | Schimmel et al. | 423/334 |
| 5,229,095 A | 7/1993 | Schimmel et al. | 423/334 |
| 5,268,156 A | 12/1993 | Schimmel et al. | 423/334 |
| 5,308,596 A | 5/1994 | Kotzian et al. | 423/333 |
| 5,318,733 A | 6/1994 | Carduck et al. | 264/15 |
| 5,382,377 A | 1/1995 | Raehse et al. | 252/174 |
| 5,417,951 A | 5/1995 | Just | 423/334 |
| 5,494,488 A | 2/1996 | Arnoldi et al. | 8/137 |
| 5,541,316 A | 7/1996 | Engelskirchen et al. | 510/471 |
| 5,580,941 A | 12/1996 | Krause et al. | 527/300 |
| 5,616,550 A | 4/1997 | Kruse et al. | 510/444 |
| 5,783,616 A | 7/1998 | Krause et al. | 524/58 |
| 5,798,328 A | 8/1998 | Kottwitz et al. | 510/438 |
| 5,830,956 A | 11/1998 | Stockhauser et al. | 526/318.2 |
| 5,847,065 A | 12/1998 | Krause et al. | 527/300 |
| 5,854,191 A | 12/1998 | Krause et al. | 510/276 |
| 5,854,321 A | 12/1998 | Krause et al. | 524/58 |

FOREIGN PATENT DOCUMENTS

| | | |
|---|---|---|
| CA | 1 036 455 | 8/1978 |
| DE | 24 12 837 | 10/1974 |
| DE | 226 012 | 8/1985 |
| DE | 39 21 839 | 1/1991 |
| DE | 42 21 381 | 2/1994 |
| DE | 43 00 772 | 7/1994 |
| DE | 43 03 320 | 11/1995 |
| DE | 44 16 438 | 11/1995 |
| DE | 44 17 734 | 11/1995 |
| DE | 196 16 770 | 1/1996 |
| DE | 44 43 177 | 6/1996 |
| DE | 195 29 905 | 2/1997 |
| DE | 195 36 082 | 4/1997 |
| DE | 196 05 688 | 8/1997 |
| DE | 196 13 103 | 10/1997 |
| DE | 196 20 411 | 10/1997 |
| DE | 196 16 693 | 11/1997 |
| DE | 196 16 767 | 11/1997 |
| DE | 196 16 769 | 11/1997 |
| DE | 196 19 221 | 11/1997 |
| DE | 196 20 267 | 11/1997 |
| DE | 197 32 751 | 2/1999 |
| EP | 0 164 514 | 12/1985 |
| EP | 0 164 552 | 12/1985 |
| EP | 0 232 202 | 8/1987 |
| EP | 0 272 030 | 6/1988 |
| EP | 0 293 753 | 12/1988 |
| EP | 0 392 592 | 10/1990 |
| EP | 0 425 427 | 5/1991 |
| EP | 0 436 835 | 7/1991 |
| EP | 0 443 651 | 8/1991 |
| EP | 0 446 982 | 9/1991 |
| EP | 0 453 003 | 10/1991 |
| EP | 0 458 397 | 11/1991 |

(List continued on next page.)

OTHER PUBLICATIONS

Applied & Environmental Microbiol. (1994), pp. 1213–1220, Tabernaro et al.

Appl. Microbiol Biotech 38 (1993), pp. 507–513, Louw et al.

Biochemica et Biophysica Acta, 384 (1975), pp. 477–483, Horikoshi et al.

"β–Glucan–spaldende Enzyme",R. Borriss; "Industrielle Enzyme", Chp. 11.5, Behr's Verlag, Hamberg, 1994, pp. 728–757.

Appl. Microbiol. Biotech 39 (1993), pp. 507–513, Louw et al.

Gene 29 (1984), pp. 21–26, Sullivan et al.

Anal.Biochem. 47 (1972), pp. 273–279, Lever. M.

Anal.Biochem 81 (1977), pp. 21–27, Lever. M.

Primary Examiner—Rebecca E. Prouty
Assistant Examiner—Manjunath N. Rao
(74) Attorney, Agent, or Firm—Stephen D. Harper; Glenn E. J. Murphy

(57) ABSTRACT

A β-Glucanase enzyme capable of hydrolytically cleaving mixed glucans is presented. The β-Glucanase is sufficiently stable under alkaline conditions for use in industrial cleaning processes, especially in the brewing industry.

18 Claims, 2 Drawing Sheets

FOREIGN PATENT DOCUMENTS

| | | |
|---|---|---|
| EP | 0 458 398 | 11/1991 |
| EP | 0 486 592 | 5/1992 |
| EP | 0 502 325 | 9/1992 |
| EP | 0 642 576 | 3/1995 |
| EP | 0 693 550 | 1/1996 |
| EP | 0 709 452 | 5/1996 |
| EP | 0 747 470 | 12/1996 |
| EP | 0 755 999 | 1/1997 |
| EP | 0 756 000 | 1/1997 |
| EP | 0 544 519 | 6/1997 |
| GB | 2 283 982 | 5/1995 |
| JP | 04/238809 | 8/1992 |
| JP | 04/260610 | 9/1992 |
| WO | WO91/02781 | 3/1991 |
| WO | WO91/02792 | 3/1991 |
| WO | WO91/08171 | 6/1991 |
| WO | WO92/06184 | 4/1992 |
| WO | WO92/18542 | 10/1992 |
| WO | WO92/21760 | 12/1992 |
| WO | WO93/16110 | 8/1993 |
| WO | WO94/02597 | 2/1994 |
| WO | WO94/02618 | 2/1994 |
| WO | WO94/05762 | 3/1994 |
| WO | WO94/18314 | 8/1994 |
| WO | WO94/23005 | 10/1994 |
| WO | WO94/23053 | 10/1994 |
| WO | WO94/27970 | 12/1994 |
| WO | WO94/28102 | 12/1994 |
| WO | WO94/28103 | 12/1994 |
| WO | WO95/00626 | 1/1995 |
| WO | WO95/07350 | 3/1995 |
| WO | WO95/14075 | 5/1995 |
| WO | WO95/27775 | 5/1995 |
| WO | WO95/14759 | 6/1995 |
| WO | WO95/17498 | 6/1995 |
| WO | WO95/22592 | 8/1995 |
| WO | WO95/23221 | 8/1995 |
| WO | WO95/35362 | 12/1995 |
| WO | WO96/16153 | 5/1996 |
| WO | WO96/23579 | 8/1996 |
| WO | WO96/23859 | 8/1996 |
| WO | WO96/23860 | 8/1996 |
| WO | WO96/23861 | 8/1996 |
| WO | WO96/34108 | 10/1996 |
| WO | WO97/12021 | 4/1997 |
| WO | WO97/13862 | 4/1997 |
| WO | WO97/19155 | 5/1997 |

| | | | | | |
|---|---|---|---|---|---|
| MKRKTFVLFS | LFTLLIGMFS | TGFANTGVVQ | AEDGRPMGST | FHETFDTFNT | 50 |
| DRWSTAGVWT | NGAMFNATWY | PEQVTISDGK | MKLQIDKEDD | EDATPEYKAG | 100 |
| ELRTNQFYQY | GLFEVNMKPA | KSTGTVSSLF | TYTGPWDWDN | DPWDEIDIEF | 150 |
| LGKDTTRVQF | NYFTNGVGNN | EHYHELGFDA | SESFNTYAFE | WRPESISWYV | 200 |
| NGELVYTATE | NIPQTPQKIM | MNLWPGIGVD | GWTGVFDGED | TPVVTEYDWV | 250 |
| RYTPLEELDN | NGEQPKPVVP | GKPEKPGKPG | KNQKNQENQE | NQKNQENQKN | 300 |
| QKIRKTSS | | | | | 308 |

Fig. 1

Fig. 2: pH profile

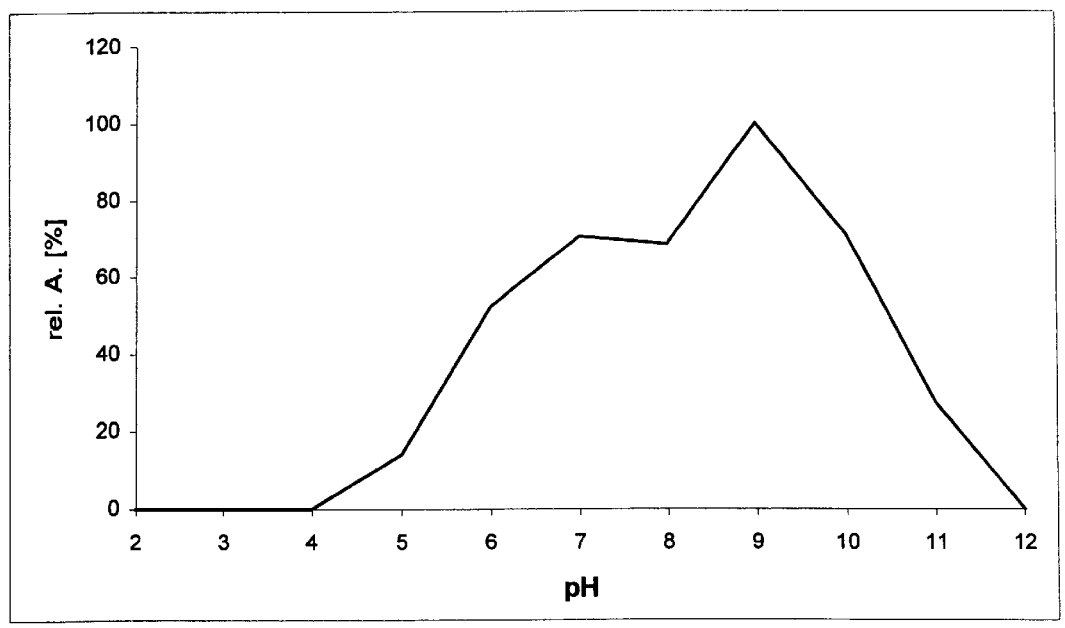

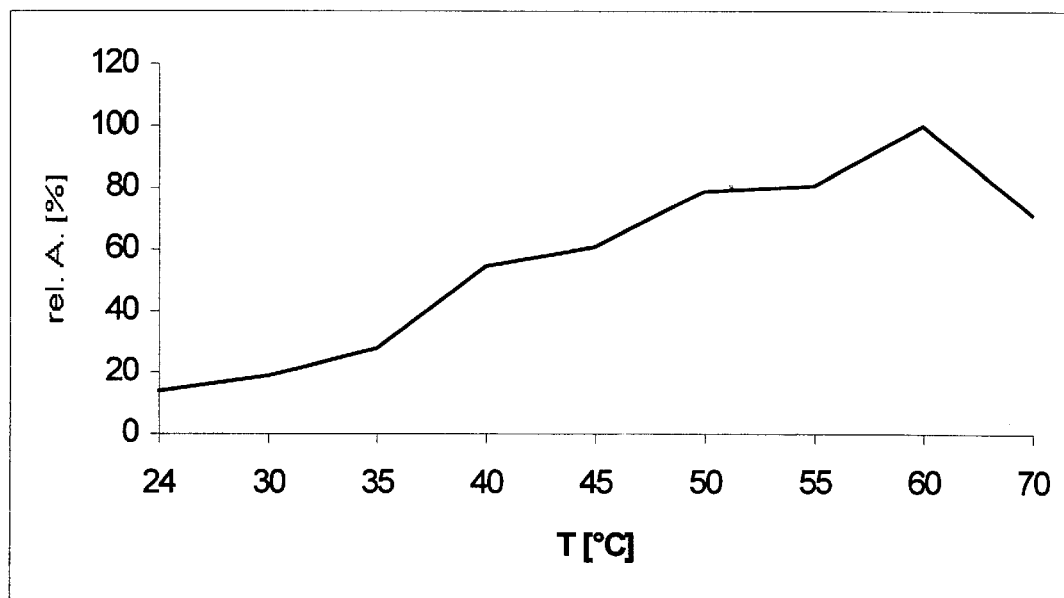
Fig. 3: Temperature profile

SEQUENCE LISTING

<160> NUMBER OF SEQ ID NOS: 2

<210> SEQ ID NO 1
<211> LENGTH: 308
<212> TYPE: PRT
<213> ORGANISM: Bacillus alkalophilus DSM 9956

<400> SEQUENCE: 1

```
Met Lys Arg Lys Thr Phe Val Leu Phe Ser Leu Phe Thr Leu Leu Ile
1               5                   10                  15

Gly Met Phe Ser Thr Gly Phe Ala Asn Thr Gly Val Val Gln Ala Glu
            20                  25                  30

Asp Gly Arg Pro Met Gly Ser Thr Phe His Glu Thr Phe Asp Thr Phe
        35                  40                  45

Asn Thr Asp Arg Trp Ser Thr Ala Gly Val Trp Thr Asn Gly Ala Met
    50                  55                  60

Phe Asn Ala Thr Trp Tyr Pro Glu Gln Val Thr Ile Ser Asp Gly Lys
65                  70                  75                  80

Met Lys Leu Gln Ile Asp Lys Glu Asp Asp Glu Asp Ala Thr Pro Glu
                85                  90                  95

Tyr Lys Ala Gly Glu Leu Arg Thr Asn Gln Phe Tyr Gln Tyr Gly Leu
            100                 105                 110

Phe Glu Val Asn Met Lys Pro Ala Lys Ser Thr Gly Thr Val Ser Ser
        115                 120                 125
```

```
Leu Phe Thr Tyr Thr Gly Pro Trp Asp Trp Asp Asn Asp Pro Trp Asp
    130                 135                 140
Glu Ile Asp Ile Glu Phe Leu Gly Lys Asp Thr Thr Arg Val Gln Phe
145                 150                 155                 160
Asn Tyr Phe Thr Asn Gly Val Gly Asn Asn Glu His Tyr His Glu Leu
                165                 170                 175
Gly Phe Asp Ala Ser Glu Ser Phe Asn Thr Tyr Ala Phe Glu Trp Arg
            180                 185                 190
Pro Glu Ser Ile Ser Trp Tyr Val Asn Gly Glu Leu Val Tyr Thr Ala
        195                 200                 205
Thr Glu Asn Ile Pro Gln Thr Pro Gln Lys Ile Met Met Asn Leu Trp
    210                 215                 220
Pro Gly Ile Gly Val Asp Gly Trp Thr Gly Val Phe Asp Gly Glu Asp
225                 230                 235                 240
Thr Pro Val Val Thr Glu Tyr Asp Trp Val Arg Tyr Thr Pro Leu Glu
                245                 250                 255
Glu Leu Asp Asn Asn Gly Glu Gln Pro Lys Pro Val Val Pro Gly Lys
            260                 265                 270
Pro Glu Lys Pro Gly Lys Pro Gly Lys Asn Gln Lys Asn Gln Glu Asn
        275                 280                 285
Gln Glu Asn Gln Lys Asn Gln Glu Asn Gln Lys Asn Gln Lys Ile Arg
    290                 295                 300
Lys Thr Ser Ser
305

<210> SEQ ID NO 2
<211> LENGTH: 927
<212> TYPE: DNA
<213> ORGANISM: Bacillus alkalophilus DSM 9956

<400> SEQUENCE: 2
atgaaaagga agacatttgt attattttct ttatttacgt tgttaattgg tatgttctca      60
acagggtttg caaatacagg tgtggttcag gcagaagatg ggagaccaat ggggtcgacg     120
tttcatgaaa cgtttgatac ctttaatacg gaccgctggt caacagctgg ggtatggaca     180
aatggagcaa tgtttaatgc gacatggtat ccagaacagg tgaccatttc agatgggaaa     240
atgaagttgc aaattgacaa ggaagatgat gaagatgcaa ccccagaata taggctggg     300
gaattaagaa cgaatcagtt ttatcaatac gggttgtttg aagtcaatat gaagccagcg     360
aaatcaacag gaaccgtctc ttcactcttt acatatacgg gtccatggga ttgggataat     420
gatccttggg atgaaatcga tattgagttc cttggaaagg atacaacaag agtccaattt     480
aactatttta ctaacggagt aggaaacaat gaacattacc acgaattagg gttcgatgca     540
tcagaatctt ttaatacgta tgcttttgaa tggagaccag aatcaattag ttggtacgta     600
aacggagaat tagtatatac agcaacagaa atatcccgc aaacaccaca aaaaattatg     660
atgaacttat ggcctggaat tggagtggat ggatggacag cgttttttga cggagaagac     720
actccagttg taacggagta tgattgggta aggtacactc cactagagga attagataat     780
aacggagaac aaccgaaacc tgtagtgcca ggaaaaccag aaaaaccagg aaaaccaggg     840
aaaaaccaga aaaccaggaa aaccaggaa accagaaaa ccaggaaaa ccagaaaac     900
caaaaaatca gaaaaccag tagttga                                          927
```

β-GLUCANASE FROM A BACILLUS

BACKGROUND OF THE INVENTION

1. Field of the Invention

This application is filed under 35 U.S.C. 371 and based on PCT/EP98/04564, filed Jul. 21, 1998.

This invention relates to an enzyme capable of hydrolytically cleaving mixed glucans, which are linked alternately by 1,3- and 1,4-β-glucosidic bonds, into oligosaccharides and to the microorganism which forms this enzyme.

Enzymes such as these belong to the class of endo-1,3-1,4-β-D-glucan4-glucanohydrolases (EC 3.2.1.73; lichenases) or endo-1.3-β-D-glucosidases (EC 3.2.1.39; laminarinases). For the purposes of the present invention, an enzyme of this type is referred to herein as β-glucanase or beta-glucanase.

2. Discussion of Related Art

Polymeric mixed glucans of the type mentioned above are present in varying amounts in virtually all cereal products. Enzymes capable of cleaving them are required above all in the food, beverage and animal feed industries, the textile industry and in the processing of starch (R. Borriss "μ-Glucan-spaltende Enzyme", in H. Ruttloff: "Industrielle Enzyme", Chapter 11.5, Behr's Verlag, Hamburg (1994)). One of the most important applications of β-glucanases is in the beverage and brewing industries where enzymes such as these are used for degrading malt and barley β-glucan. The enzymes used for this purpose normally emanate from *Bacillus subtilis*, as described for example in German patent DD 226 012 A1, or from *Bacillus amyloliquefaciens*, although β-glucanases from other microorganisms, for example *Achromobacter lunatus, Athrobacter luteus, Aspergillus aculeatus, Aspergillus niger, Disporotrichum dimorphosporum, Humicola insolens, Penicillium emersonli, Penicillium funiculosum* or *Trichoderma reesei*, are also known. A commercial product intended for use in the brewing industry is marketed, for example, under the name of Cereflo® (manufacturer: Novo Nordisk A/S).

Hitherto known β-glucanases have pH optima in the weakly acidic to neutral range, so that their use is confined to processes which are carried out at those pH values. The problem addressed by the present invention was to extend the field of application of β-glucanases and to develop a β-glucanase which would be sufficiently stable under alkaline conditions for use in industrial processes carried out under conditions.

DESCRIPTION OF THE DRAWINGS

FIG. 1 depicts in one-letter code the amino acid sequence of the β-glucanase according to the invention (SEQ ID-NO.:1) obtained from *Bacillus alkalophilus* DSM 9956.

FIG. 2 depicts glucanolytic activity as a function of pH for the β-glucanase obtained from *Bacillus alkalophilus* DSM 9956 in Example 1 below.

FIG. 3 depicts depicts glucanolytic activity as a function of temperature for the β-glucanase obtained from *Bacillus alkalophilus* DSM 9956 in Example 1 below.

DESCRIPTION OF THE INVENTION

The present invention relates to an enzyme obtainable from *Bacillus alkalophilus* DSM 9956 which has the glucanolytic activity mentioned at the beginning, to the microorganism Bacillus alkalophilus DSM 9956 which produces a β-glucanase and to the gene encoding the ,β-glucanase from *Bacillus alkalophilus* DSM 9956 which was identified and sequenced (SEQ ID-NO.:2) in the course of the work culminating in the present invention. If desired, this gene may be cloned in known manner in other bacteria and the β-glucanase may be expressed there. Accordingly, the present invention also relates to host organisms containing the said gene obtainable by essentially microbiological processes. The amino acid sequence—derived from the sequence of the β-glucanase gene from *Bacillus alkalophilus* DSM 9956—of the β-glucanase according to the invention obtainable from that microorganism (SEQ ID-NO.:1) is shown in the one-letter code in FIG. 1. The β-glucanase from *Bacillus alkalophilus* DSM 9956, including the signal peptide, which is split off by a signal peptidase after transport through the cell wall of the microorganism and which, according to comparisons with data known from the literature [M.E. Louw, S. J. Reid, Watson, Appl. Microbiol. Biotech. 39 (1993), 507–513], presumably comprises 31 amino acids, consists of 308 amino acids. The corresponding microorganism is gram-positive, its cell form is rodlet-like (width ca. 0.7 μm to 0.9 μm, length ca. 2.5 μm to 4.0 μm); it was deposited by applicants on 13.04.1995 in the DSM—Deutsche Sammiung von Mikrooganismen und Zellkulturen GmbH, Mascheroder Weg 1b, 38124 Braunschweig, and has been given the number DSM 9956.

A β-glucanase according to the invention preferably has a homology of more than 70%, more particularly 75% to 99%, to the β-glucanase from *Bacillus alkalophilus* DSM 9956. The same applies to the basic gene.

The enzyme according to the invention is preferably used in the food industry, more especially in the beverage and brewing industry, more particularly for removing glucan and/or lichenan in the cleaning of membranes and other equipment in those industries.

The present invention also relates to a process for removing glucan and/or lichenan in the cleaning of membranes and other equipment in the food industry, more particularly the brewing industry, using a β-glucanase according to the invention.

EXAMPLES

Example 1

Chromosomal DNA from *Bacillus alkalophilus* C/M2-3 was partly digested with Sau3A and a fraction of 4 to 8 kb large fragments was isolated by gel electrophoresis. After ligation into the BamH1-site of the plasmid pMK4, an *E. coli*—Bacillus shuttle vector [M. A. Sullivan et al., Gene 29 (1984), 21–26], it was transformed into competent *E. coli* DH5α cells. Recombinant clones with β-glucanase activity were identified by coloring with Congo Red on LB plates containing 0.2% lichenin (pH 8.5).

The β-glucanase was purified from the cell supernatant of a clone in *E. coli* DH5α pmK4. After dialysis of the cell-free supernatant against 20 mM sodium phosphate buffer (pH 7.5), the dialyzate was fixed to Q-Sepharose (Pharmacia) and eluted with a linear gradient of 0–1 M NaCl in 25 mM sodium phosphate buffer (pH 7.5 or pH 9.0).

The detection and determination of the glucanolytic activity was based on modifications of the process described by M. Lever in Anal. Biochem. 47 (1972), 273–279 and Anal Biochem. 81 (1977), 21–27. A 0.5% by weight solution of β-glucan (Sigma No. G6513) in 50 mM glycine buffer (pH 9.0) was used for this purpose. 250 μl of this solution are added to 250 μl of a solution containing the agent to be tested for glucanolytic activity and incubated for 30 minutes at 40° C. 1.5 ml of a 1% by weight solution of p-hydroxybenzoic acid hydrazide (PAHBAH) in 0.5 M NaOH, which contains 1 mM bismuth nitrate and 1 mM potassium sodium tartrate, are then added, after which the solution is heated for 10 minutes to 70° C. After cooling (2 minutes/0° C.), the absorption at 410 nm is determined against a blank value at room temperature (for example with a Uvikon® 930 photometer) using a glucose calibration curve. The blank value is a solution which is prepared in the same way as the measuring solution except that the glucan solution is added after the PAHBAH solution. 1 U corresponds to the quantity of enzyme which produces 1 μmole of glucose per minute under these conditions.

The specific activity of the enzyme thus obtained amounted to 4390 mU per mg protein whereas the activity of the starting solution was lower by a factor of 152. The enzyme was colored (silver coloring) as a homogeneous band in SDS polyacrylamide gel electrophoresis.

With the aid of marker proteins (cytochrome c, equine myoglobin, chymotrypsinogen, ovalbumin, bovine serum albumin) as an internal standard, the molecular weight of the β-glucanase from *Bacillus alkalophilus* DSM 9956 was estimated by SDS polyacrylamide gel electrophoresis to be about 30,000.

In isoelectronic focusing (pH 3 to 9), the isoelectric point of the β-glucanase was found by activity coloring to be at pH 5.2.

EXAMPLE 2 pH Profile

The determination of glucanolytic activity at various pH values was carried but in a Davies universal buffer (21.01 g citric acid . $H_2O$, 13.61 g $KH_2PO_4$, 19.07 g $Na_2B_4O_7$. 10 $H_2O$, 12.11 g tris and 7.46 g KCl in 1 l dist. water; 50 ml of this stock solution are adjusted to the required pH with 0.4 N NaOH and made up with dist. water to 200 ml) at 40° C. after incubation for 30 minutes. As can clearly be seen from the pH profile shown in FIG. 2 (relative glucanolytic activity, rel. A., plotted against the pH), the enzyme is at its most active between pH 6 and pH 10.5. The optimum lies at pH 9.

EXAMPLE 3

Temperature Profile

The dependence on temperature of the glucanolytic activity of the β-glucanase obtained from *Bacillus alkalophilus* DSM 9956 was measured in glycine/NaOH at pH 9 after incubation for 15 minutes. The pH value of the test solution was adapted because the buffer has a dependence on temperature of ca. pH 0.033 per °C. The maximum of the glucanolytic activity is at 60° C., as shown in FIG. 3 where the relative glucanolytic activity (rel. A.) of the enzyme is plotted against the temperature (T).

Statement Under 37 C.F.R. §§ 1.821(f) and (g)

The contents of the attached paper Sequence Listing and its computer-readable form are the same and add no new matter in this application.

What is claimed is:

1. A biologically pure culture of β-Glucanase-producing microorganism *Bacillus alkalophilus* DSM 9956.

2. An isolated polypeptide with β-glucanolytic activity having the amino acid sequence SEQ ID NO:1.

3. An isolated polynucleotide which encodes the polypeptide of claim 2.

4. An isolated polynucleotide comprising the sequence SEQ ID NO:2 or a polynucleotide with more than 70 percent homology to SEQ ID NO:2, wherein said polynucleotide encodes a polypeptide with β-glucanolytic activity.

5. The polynucleotide of claim 4 which is 75 to 99 percent homologous to the sequence reproduced in SEQ ID-NO:2.

6. A host microorganism transformed with the polynucleotide of claim 3.

7. An isolated polypeptide with β-glucanolytic activity and a homology of more than 70 percent to the polypeptide with the amino acid sequence SEQ ID NO:1.

8. The polypeptide of claim 7 with a homology of 75 to 99 percent to the polypeptide with the amino acid sequence SEQ ID NO:1.

9. An isolated polynucleotide which encodes the polypeptide of claim 7.

10. The polynucleotide of claim 9 with SEQ ID NO:2 or a polynucleotide with more than 70 percent homology to that sequence.

11. The polynucleotide of claim 10 with a homology of 75 to 99 percent to SEQ ID NO:2.

12. A host microorganism transformed with the polynucleotide of claim 9.

13. A process for cleaning membranes and equipment in the food industry comprising contacting membranes and equipment with the polypeptide of claim 2.

14. The process of claim 13 wherein said membranes and equipment are used in the brewing industry.

15. The process of claim 13 wherein said enzyme aids in the removal of glucan and/or lichenan.

16. A process for cleaning membranes and equipment in the food industry comprising contacting membranes and equipment with the polypeptide of claim 7.

17. The process of claim 15 wherein said membranes and equipment are used in the brewing industry.

18. The process of claim 16 wherein said enzyme aids in the removal of glucan and/or lichenan.

* * * * *